United States Patent [19]

Bergemann

[11] Patent Number: 5,491,293

[45] Date of Patent: *Feb. 13, 1996

[54] INBRED CORN LINE LH225

[75] Inventor: Scott Bergemann, Stanton, Minn.

[73] Assignee: Holden's Foundation Seeds Inc., Williamsburg, Iowa

[*] Notice: The term of this patent shall not extend beyond the expiration date of Pat. No. 5,416,255.

[21] Appl. No.: 342,688

[22] Filed: Nov. 21, 1994

Related U.S. Application Data

[63] Continuation of Ser. No. 140,371, Oct. 21, 1993, Pat. No. 5,416,255.

[51] Int. Cl.$^6$ .............................. A01H 5/00; A01H 1/02
[52] U.S. Cl. ................. 800/200; 800/250; 800/DIG. 56; 47/58; 47/DIG. 1
[58] Field of Search ...................... 800/200, 250, 800/DIG. 56; 47/58.03, 58.05, DIG. 1

[56] References Cited

U.S. PATENT DOCUMENTS 5,285,003  2/1994  Harper ..................................... 800/200

OTHER PUBLICATIONS

Wych, 1988 In Corn and Corn Improvement, Sprague et al., eds. Ch. 9: 565–607.

*Primary Examiner*—Gary Benzion
*Assistant Examiner*—Erich E. Veitenheimer
*Attorney, Agent, or Firm*—Henderson & Sturm

[57] ABSTRACT

An inbred corn line, designated LH225, is disclosed. The invention relates to the seeds of inbred corn line LH225, to the plants of inbred corn line LH225 and to methods for producing a corn plant produced by crossing the inbred line LH225 with itself or another corn line. The invention further relates to hybrid corn seeds and plants produced by crossing the inbred line LH225 with another corn line.

4 Claims, No Drawings

INBRED CORN LINE LH225

This application is a continuation of application Ser. No. 08/140,371, filed Oct. 21, 1993, now U.S. Pat. No. 5,416,255.

BACKGROUND OF THE INVENTION

The present invention relates to a new and distinctive corn inbred line, designated LH225. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations, Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et at., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop stable, high yielding corn hybrids that are agronomically sound. The reasons for this goal are obviously to maximize the amount of grain produced on the land used and to supply food for both animals and humans. To accomplish this goal, the corn breeder must select and develop corn plants that have the traits that result in superior parental lines for producing hybrids.

SUMMARY OF THE INVENTION

According to the invention, there is provided a novel inbred corn line, designated LH225. This invention thus relates to the seeds of inbred corn line LH225, to the plants of inbred corn line LH225 and to methods for producing a corn plant produced by crossing the inbred line LH225 with itself or another corn line. This invention further relates to hybrid corn seeds and plants produced by crossing the inbred line LH225 with another corn line.

DEFINITIONS

In the description and tables which follow, a number of terms are used. In order to provide a clear and consistent understanding of the specification and claims, including the scope to be given such terms, the following definitions are provided:

Predicted RM. This trait for a hybrid, predicted relative maturity (RM), is based on the harvest moisture of the grain. The relative maturity rating is based on a known set of checks and utilizes conventional maturity systems such as the Minnesota Relative Maturity Rating System.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Yield (Bushels/Acre). The yield in bushels/acre is the actual yield of the grain at harvest adjusted to 15.5% moisture.

Moisture. The moisture is the actual percentage moisture of the grain at harvest.

GDU Silk. The GDU silk (=heat unit silk) is the number of growing degree units (GDU) or heat units required for an inbred line or hybrid to reach silk emergence from the time of planting. Growing degree units are calculated by the Barger Method, where the heat units for a 24-hour period are:

$$GDU = \frac{(\text{Max.} + \text{Min})}{2} - 50.$$

The highest maximum used is 86° F. and the lowest minimum used is 50° F. For each hybrid, it takes a certain number of GDUs to reach various stages of plant development. GDUs are a way of measuring plant maturity.

Stalk Lodging. This is the percentage of plants that stalk lodge, i.e., stalk breakage, as measured by either natural lodging or pushing the stalks determining the percentage of plants that break off below the ear. This is a relative rating of a hybrid to other hybrids for standability.

Root Lodging. The root lodging is the percentage of plants that root lodge; i.e., those that lean from the vertical axis at an approximate 30° angle or greater would be counted as root lodged.

Plant Height. This is a measure of the height of the hybrid from the ground to the tip of the tassel, and is measured in centimeters.

Ear Height. The ear height is a measure from the ground to the ear node attachment, and is measured in centimeters.

Dropped Ears. This is a measure of the number of dropped ears per plot, and represents the percentage of plants that dropped an ear prior to harvest.

DETAILED DESCRIPTION OF THE INVENTION

Inbred corn line LH225 is a yellow dent corn with superior characteristics, and provides an excellent parental line in crosses for producing first generation ($F_1$) hybrid corn.

Inbred corn line LH225 was developed from the single cross CM105×B37 by selfing and using an ear-row pedigree method of breeding. Selfing and selection were practiced within the above $F_1$ cross for seven generations in the development of LH225. Some of the criteria used to select ears in various generations include: yield, stalk quality, root quality, disease tolerance, late plant greenness, late season plant intactness, ear retention, pollen shedding ability, silking ability, and corn borer tolerance. During the development of the line, crosses were made to inbred testers for the purpose of estimating the line's general and specific combining ability, and evaluations were run by the Stanton, Minnesota Research Station. The inbred was evaluated further as a line and in numerous crosses by the Stanton and other research stations across the Corn Belt. The inbred has proven to have a very good combining ability in hybrid combinations.

The inbred has shown uniformity and stability for all traits, as described in the following variety description information. It has been self-pollinated and ear-rowed a sufficient number of generations, with careful attention to uniformity of plant type to ensure homozygosity and phenotypic stability. The line has been increased both by hand and sibbed in isolated fields with continued observation for uniformity. No variant traits have been observed or are expected in LH225.

Inbred corn line LH225 has the following morphologic and other characteristics (based primarily on data collected at Williamsburg, Iowa):

VARIETY DESCRIPTION INFORMATION

A. Maturity
   INBRED=LH225
   Best Adapted For: Northcentral Regions of the Corn Belt
   Heat Unit Silk: 1360

$$\text{Heat Units:} = \frac{[\text{Max. Temp. } (\leq 86 \cdot \text{F.}) + \text{Min. Temp. } (\geq 50 \cdot \text{F.})]}{2} - 50$$

B. Plant Characteristics
   Plant height (to tassel tip): 199 cm.
   Length of top ear internode: 14 cm.
   Number of tillers: None
   Cytoplasm type: Normal
   Ear height (to base of top ear): 71 cm.
   Number of ears per stalk: Single
C. Leaf
   Color: 5 GY ¾ Munsell Color Charts for Plant Tissues
   Angle from stalk: <30°
   Marginal waves: Many
   Width (widest point of ear node lead: 10 cm.
   Number of leaves (mature plants): 13
   Sheath pubescence: Heavy
   Longitudinal creases: Few
   Length (ear node leaf): 68 cm.
D. Tassel
   Number of lateral branches: 4
   Branch angle from central spike: 30°–40°
   Pollen shed: Medium
   Anther color: Dark Purple
   Glume color: Green with brown margin
   Peduncle length (top leaf to basal branch): 9 cm.
E. Ear (Husked Ear Data Except When Stated Otherwise)
   Length: 15 cm.
   Midpoint diameter: 38 mm.
   Weight: 71 gm.
   Kernel Rows: Distinct, Straight
   Number of Kernel rows: 14
   Silk color: Green
   Husk color (fresh): Light green
   Husk color (dry): Buff
   Husk extension: Long
   Shank length: 12 cm.
   Shank (no. of internodes): 8
   Taper of Ear: Average
   Husk leaf: <8 cm.
   Position of shank (dry husks): Upright
F. Kernel (Dried)
   Size (from ear midpoint)
   Length: 12 mm.
   Width: 8 mm.
   Thickness: 4 min.
   Shape grade (% rounds): >80
   Pericarp color: Variegated: bronze at the pedicel becoming colorless at the crown
   Aleurone color: White
   Endosperm color: Yellow
   Endosperm type: Normal starch
   Gm Weight/100 seeds (unsized): 24 gm.
G. Cob
   Diameter at midpoint: 30 mm.
   Strength: Strong
   Color: Red This invention is also directed to methods for producing a corn plant by crossing a first parent corn plant with a second parent corn plant, wherein the first or second corn plant is the inbred corn plant from the line LH225. Further, both first and second parent corn plants may be from the inbred line LH225. Therefore, any methods using the inbred corn line LH225 are part of this invention: selfing, backcrosses, hybrid breeding, and crosses to populations. Any plants produced using inbred corn line LH225 as a parent are within the scope of this invention. Advantageously, the inbred corn line is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

Tissue culture of corn is described in European Patent Application, Publication No. 160,390, incorporated herein by reference. Corn tissue culture procedures are also described in Green and Rhodes, "Plant Regeneration in Tissue Culture of Maize", *Maize for Biological Research* (Plant Molecular Biology Association, Charlottesville, Va. 1982), at 367–372. Thus, another aspect of this invention is to provide for cells which upon growth and differentiation produce the inbred line LH225.

The closest related art to LH225 is the corn line LH146. As a line LH225 has specific combining ability with LH82 and possibly LH82 derivatives. When in combination with LH82, LH225 has very rapid dry down. This is unexpected due to the lateness of B37 which theoretically makes up one half of LH225's genetic makeup. B37 is a line that historically was used in the extreme Southern corn growing areas and the South Central corn growing areas (e.g. Southeastern United States, Southern Indiana, Southern Ohio, etc.). LH225 is adapted to the more Northern corn growing areas.

Table 1 shows the interpretation of disease ratings and Table 2 shows head to head comparisons of LH225 versus LH146 in hybrid combinations. Column 2 of Table 1 indicates the pedigrees tested and column 4 shows the total number of geographical locations where these pedigrees were compared. Column 5 (#1 Hybrid Mean) shows the mean values of the first genotype listed in column 2. Column 6 indicates the trait or characteristics (Yield, Moisture, Stalk Lodging and Root Lodging). Column 7 shows the difference between the first genotype listed in column 2 versus the second genotype (Genotype #1 minus Genotype #2). Column 8 shows the statistical probability and column 9 indicates general notes on the comparison.

TABLE 1

INTERPRETATION OF DISEASE RATINGS

Rating

0 = 0% of the plant showing lesions
1 = Less than 5% of the plant covered with lesions
2 = Less than 10% of the plant covered with lesions
3 = Less than 30% of the plant covered with lesions
4 = Less than 40% of the plant covered with lesions
5 = Less than 50% of the plant covered with lesions
6 = Less than 60% of the plant covered with lesions
7 = Less than 70% of the plant covered with lesions
8 = Less than 80% of the plant covered with lesions
9 = 80–100% of the plant covered with lesions Comparison 3 compares LH225 with LH146 in another cross involving an LH82 derivative which is LH165. The parents of LH165 are LH82 and LH51. LH225 again contributed a significant yield advantage over LH146 in the hybrid combination. In this case, however, there was substantially more grain moisture associated with the LH225× LH165 cross. Grain moisture and dry down are traits that are complexly inherited and unpredictable. Compared to the line LH146, LH225 contributed to higher moisture when crossed to LH165. The relative magnitude of this moisture difference and that which was demonstrated with LH82 (comparison 1 and 2) is surprising. These two hybrids (comparison 1, 2, and 3) demonstrate quite different patterns for grain moisture dry down between LH225 and LH 146.

TABLE 2

LH225 - Head to Head Comparisons

| Comparison No. | Pedigrees Compared | Year | Loc. | #1 Hybrid Mean | Trait | Diff. | Prob. | Notes |
|---|---|---|---|---|---|---|---|---|
| 1 | LH225 × LH82 | 1991 | 17 | 177.65 | Yield | +22.647 | .000 | |
| | LH146 × LH82 | | 17 | 18.09 | Mst | +0.729 | .026 | |
| | | | 17 | 5.47 | Stalk | +0.882 | .484 | |
| | | | 16 | 0.19 | Root | +0.063 | .333 | |
| 2 | LH225 × LH82 | 1992 | 57 | 178.53 | Yield | +18.877 | .000 | |
| | LH146 × LH82 | | 57 | 22.95 | Mst | +0.422 | .028 | |
| | | | 57 | 5.46 | Stalk | +0.596 | .363 | |
| | | | 57 | 0.93 | Root | −0.596 | .198 | |
| 3 | LH225 × LH165 | 1992 | 15 | 168.47 | Yield | +7.133 | .038 | |
| | LH146 × LH165 | | 15 | 24.02 | Mst | +3.175 | .000 | |
| | | | 15 | 1.607 | Stalk | −1.067 | .340 | |
| | | | 15 | 0.00 | Root | −0.467 | .131 | |
| 4 | LH225 × LH167 | 1992 | 11 | 171.64 | Yield | +19.091 | .004 | |
| | LH146 × LH82 | | 11 | 23.68 | Mst | +1.470 | .012 | |
| | | | 11 | 2.00 | Stalk | 0.000 | 1.00 | |
| | | | 11 | 0.00 | Root | −0.091 | .341 | |
| 5 | LH225 × LH85 | 1992 | 8 | 165.13 | Yield | −2.375 | .446 | |
| | LH146 × LH82 | | 8 | 19.15 | Mst | −1.224 | .074 | |
| | | | 8 | 1.50 | Stalk | −1.000 | .316 | |
| | | | 8 | 0.25 | Root | +0.125 | .351 | |
| 6 | LH225 × LH82 | 1991 | 16 | 177.81 | Yield | +9.688 | .047 | |
| | P3751 | | 16 | 17.98 | Mst | +0.383 | .085 | |
| | | | 16 | 5.38 | Stalk | +0.750 | .560 | |
| | | | 15 | 0.20 | Root | +0.067 | .334 | |
| 7 | LH225 × LH82 | 1992 | 57 | 178.53 | Yield | −2.158 | .363 | |
| 8 | P3751 | | 57 | 22.95 | Mst | −0.195 | .378 | |
| | | | 57 | 5.46 | Stalk | +3.667 | .000 | |
| | | | 57 | 0.93 | Root | −0.018 | .948 | |

Comparison 1 and 2 compares LH225×LH82 versus LH146×LH82. LH146 ×LH82 has been used extensively in the Northern corn growing areas such as New York and Minnesota. LH146 whose parentage includes CM105 and B73 (three-fourths CM105 and one-fourth B73) is a line that has realized large usage in these Northern corn growing areas. LH146 is the closest commercially used line to the new invention LH225. In each of two years, the hybrid LH225×LH82 had a highly significant yield advantage to the commercial hybrid LH146×LH82 (22 bushels/acre in 1991 and 19 bushels/acre in 1992). The grain moisture was slightly higher (0.7% and 0.4% in 1991 and 1992 respectively), but this is much lower than a plant breeder would anticipate given the parentage of LH225. Further, this moisture disadvantage is not substantial when consideration is given to the magnitude of the yield advantages.

The remaining comparisons (comparisons 4, 5, 6, and 7) show the performance of LH225 in hybrid combinations compared to competitive hybrids that are used in the same areas to which the LH225 crosses are adapted. LH225× LH167 compared to LH146×LH82 (comparison 4), had significantly and substantially higher yield (19 bushels/acre) and more moisture. LH225×LH85 compared to LH146× LH82 (comparison 5) had equal yield, but in this case significant and substantially lower grain moisture. In comparisons 6 and 7, LH225×LH82 is compared to the very widely grown hybrid Pioneer Brand 3751 in both 1991 and 1992. In 1991, LH225 ×LH82 had significantly higher yield than 375 1 and equal grain moisture. In 1992, yield and moisture were the same but LH225×LH82 had somewhat more stalk lodging. LH225×LH82 is phenotypically very diverse from the hybrid Pioneer brand 3751 (genetic diversity is assumed by a breeder skilled in the art but the exact parentage of 3751 has not been publically disclosed). In each of these comparisons (comparisons 4, 5, 6, and 7), the LH225 cross had value beyond that of the competitive hybrid 3751 for yield, grain dryness, and genetic diversity.

DEPOSIT INFORMATION

Inbred seeds of LH225 have been placed on deposit with the American Type Culture Collection (ATCC), Rockville, Md. 20852, under Deposit Accession Number 75565 on Oct. 6, 1993. A Plant Variety Protection Certificate is being applied for with the United States Department of Agriculture.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method for producing first generation ($F_1$) hybrid corn seed, said seed being capable of producing a hybrid corn plant having the characteristics of wide leaves, robust plant type, and consistent and superior hybrid grain yield and dry down when compared to elite hybrids used in the northern corn region, comprising crossing a first inbred parent corn plant with a second inbred parent corn plant and harvesting the resultant first generation ($F_1$) hybrid corn seed, wherein said first or second parent corn plant is the corn plant of LH225, the seed of which have been deposited and have ATCC Accession No. 75565.

2. The method of claim 1 wherein the corn plant LH225, the seed of which have been deposited and have ATCC Accession No. 75565, is the female parent.

3. The method of claim 1 wherein the corn plant LH225, the seed of which have been deposited and have ATCC Accession No. 75565, is the male parent.

4. A first generation ($F_1$) hybrid corn plant produced by growing said hybrid corn seed of claim 1.

* * * * *